(12) United States Patent
Iwasaki

(10) Patent No.: US 8,581,972 B2
(45) Date of Patent: Nov. 12, 2013

(54) ENDOSCOPIC APPARATUS AND CONTROL METHOD FOR ENDOSCOPIC APPARATUS

(75) Inventor: Tomoki Iwasaki, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 1058 days.

(21) Appl. No.: 11/901,908

(22) Filed: Sep. 19, 2007

(65) Prior Publication Data

US 2008/0074492 A1  Mar. 27, 2008

(30) Foreign Application Priority Data

Sep. 22, 2006 (JP) ................. 2006-257783

(51) Int. Cl.
*A61B 1/04* (2006.01)
(52) U.S. Cl.
USPC .............................. 348/68; 600/101; 600/178
(58) Field of Classification Search
USPC ......................................................... 348/68
See application file for complete search history.

(56) References Cited

U.S. PATENT DOCUMENTS

| 6,943,822 B2* | 9/2005 | Iida et al. .................. 348/65 |
| 7,898,669 B2* | 3/2011 | Kim et al. .................. 356/486 |
| 2003/0063188 A1 | 4/2003 | Takahashi et al. | |

FOREIGN PATENT DOCUMENTS

| JP | 11-298907 | | 10/1999 |
| JP | 2003-265410 | | 9/2003 |
| JP | 2005-034166 A | * | 2/2005 |
| JP | 2005-131363 | | 5/2005 |
| JP | 2005-349142 | | 12/2005 |

* cited by examiner

*Primary Examiner* — Kevin Bates
(74) *Attorney, Agent, or Firm* — Scully, Scott, Murphy & Presser, P.C.

(57) ABSTRACT

According to the invention, a processor CPU includes a scope information extracting section, a light source information extracting section, a main white balance searching section, a sub-white-balance extracting section, a main white balance update section, a sub-white-balance update section, and an image processing control section.

12 Claims, 17 Drawing Sheets

FIG.2

| |
|---|
| AREA 1: Serial No.={Scope Serial Number Data=Scope ID} |
| AREA 2: Name={Scope Model Name Data} |
| AREA 3: Size={Scope Distal End Diameter and Forceps Diameter Data} |
| AREA 4: CCD Type={CCD-Related Information Data} |
| AREA 5: Number Of Times Of Energization={Data on Total Number Of Times Of Energization in Scope} |
| AREA 6: User Comment={Arbitrary User-Inputted Comment Data} |
| AREA 7: First Examination Date={First Used Date Data} |
| AREA 8: Warranty Expiration Date={Scope Warranty Expiration Data} |
| AREA 9: Service Comment={Arbitrary Serviceman-Inputted Comment Data} |
| AREA 10: Factory Comment={Arbitrary Manufacturing Factory-Inputted Comment Data} |
| AREA 11: Reprocess Information={Reprocess (Cleaning) Information Data} |
| AREA 12: Number of Times of Inspection={Data on Total Number Of Times Of Inspection} |
| AREA 13: Version Information={Contained Software Version Data} |
| AREA 14: Sub-White-Balance={White Balance Data } |

| |
|---|
| AREA 1: Serial No.={Scope Serial Number Data=Scope ID} |
| AREA 2: Name={Scope Model Name Data} |
| AREA 3: Size={Scope Distal End Diameter and Forceps Diameter Data} |
| AREA 4: CCD Type={CCD-Related Information Data} |
| AREA 5: Number Of Times Of Energization={Data on Total Number Of Times Of Energization in Scope} |
| AREA 6: User Comment={Arbitrary User-Inputted Comment Data} |
| AREA 7: First Examination Date={First Used Date Data} |
| AREA 8: Warranty Expiration Date={Scope Warranty Expiration Data} |
| AREA 9: Service Comment={Arbitrary Serviceman-Inputted Comment Data} |
| AREA 10: Factory Comment={Arbitrary Manufacturing Factory-Inputted Comment Data} |
| AREA 11: Reprocess Information={Reprocess (Cleaning) Information Data} |
| AREA 12: Number of Times of Inspection={Data on Total Number Of Times Of Inspection} |
| AREA 13: Version Information={Contained Software Version Data} |
| AREA 14: Sub-White-Balance={White Balance Data } |
| AREA 15: Main White Balance Data Area={White Balance Data Associated With Light Source Information}<br><br>1) White Balance Data on First Light Source<br>2) White Balance Data on Second Light Source<br>⋮<br>i) White Balance Data on $i^{th}$ Light Source<br>j) White Balance Data on $j^{th}$ Light Source |

| SCOPE DATA |
|---|
| SCOPE ID=ES01 |
| WHITE BALANCE DATA OF LIGHT SOURCE ID=K01 |
| WHITE BALANCE DATA OF LIGHT SOURCE ID=K02 |
| WHITE BALANCE DATA OF LIGHT SOURCE ID=K03 |
| WHITE BALANCE DATA OF LIGHT SOURCE ID=K04 |
| |

| SETTING DATA |
|---|
| WHITE BALANCE DATA OF SCOPE ID=ES01 |
| WHITE BALANCE DATA OF SCOPE ID=ES02 |
| WHITE BALANCE DATA OF SCOPE ID=ES03 |
| |

243

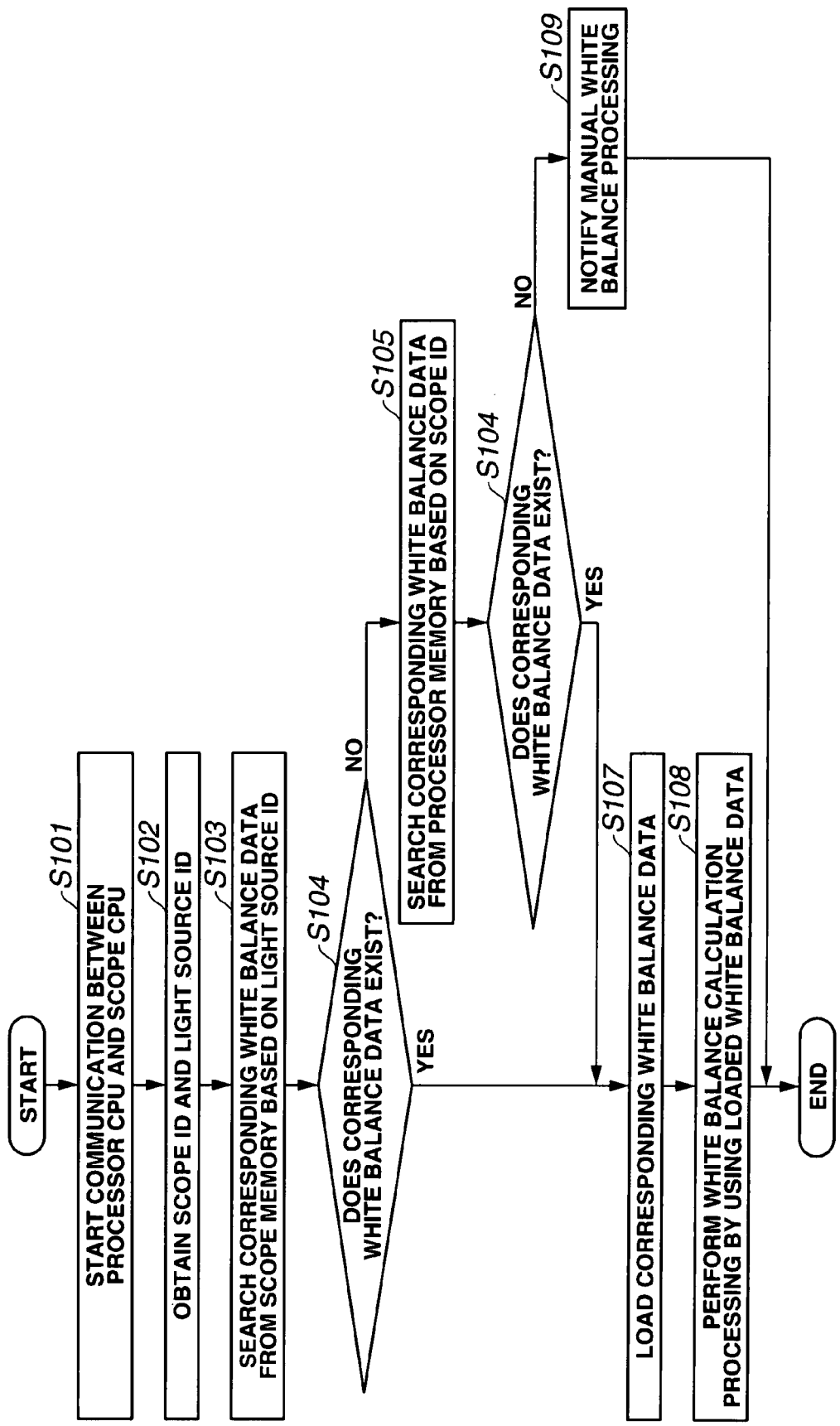

ENDOSCOPIC APPARATUS AND CONTROL METHOD FOR ENDOSCOPIC APPARATUS

This application claims benefit of Japanese Application No. 2006-257783 filed in Japan on Sep. 22, 2006, the contents of which are incorporated by this reference.

BACKGROUND OF THE INVENTION

1. Field of the Invention

The present invention relates to an endoscopic apparatus that automatically performs white balance processing and a control method for an endoscopic apparatus.

2. Description of the Related Art

Conventionally, in an electronic endoscopic apparatus, white balance processing is performed for adjusting a variation in color reproducibility due to a variation in sensitivity of a solid image pickup device or a spectral variation of observation light outputted from a light source device.

Conventional white balance processing performs white balance adjustment by adjusting R and B gain values such that image signals of red (R), green (G) and blue (B) read out from an image pickup device that has picked up an image of a white subject can have a ratio of 1:1:1. The white balance values (R and B gain values) defined by the white balance adjustment are recorded in a processor and are used when an electronic endoscopic apparatus is used thereafter.

In other words, when a video scope is connected to an electronic endoscopic apparatus, the electronic endoscopic apparatus loads and defines white balance values corresponding to the video scope. Then, gain control based on the white balance values is performed on the image signals loaded from the image pickup device.

For example, Japanese Unexamined Patent Application Publication No. 2005-131363 discloses an endoscopic apparatus including a scope 210, a light source 220 and a processor 240, as shown in FIG. 18. The scope 210 has a CCD 211 at the distal end of an insertion section thereof. The CCD 211 is a solid image pickup device. The light source 220 supplies illumination light from a lamp 221 to the scope 210 through a light guide 212. The processor 240 performs signal processing on image pickup signals picked up by the CCD 211 by an image processing section 241 and causes an endoscopic image thereof to be displayed on a monitor 230.

In Japanese Unexamined Patent Application Publication No. 2005-131363, a scope memory 214 provided in the scope 210 stores scope data (such as insertion diameter and specifications of the CCD) of the scope and a scope ID, which is identification information for identifying the scope, and white balance data associated by a light source ID of the light source 220, which has been connected thereto in the past, as shown in FIG. 19.

A processor memory 243 including a backup RAM or the like in the processor 240 stores setting data relating to processing in the processor 240 and white balance data associated by the scope ID of the scope 210 and the like, which has been connected in the past, as shown in FIG. 20.

The endoscopic apparatus having such a configuration as disclosed in Japanese Unexamined Patent Application Publication No. 2005-131363 performs auto white balance processing as shown in FIG. 21. In other words, the processor 240, scope 210 and light source 220 are connected. Upon powering on these devices, the processor CPU 242 within the processor 240 in step S101 starts communication with the scope CPU 213 within the scope 210, as shown in FIG. 21.

Then, the processor CPU 242 in step S102 obtains the scope ID from the scope memory 214 through the scope CPU 213 and obtains the light source ID, which is identification information for identifying a light source, from a light source memory 222 within the light source 210.

Next, the processor 242 in step S103 searches white balance data corresponding to the light source ID from the scope memory 214 through the scope CPU 213 based on the light source ID.

Then, the processor CPU 242 in step S104 determines whether corresponding white balance data exists within the scope memory 214 or not based on the search result information from the scope CPU 213.

If it is determined that corresponding white balance data exists within the scope memory 214, the processor CPU 242 in step S107 loads the corresponding white balance data from the scope memory 214 through the scope CPU 213.

On the other hand, if it is determined that no corresponding white balance data exists within the scope memory 214, the processor CPU 242 in step S105 searches white balance data corresponding to the scope ID from the processor memory 243 based on the scope ID.

Then, the processor CPU 242 in step S106 determines whether corresponding white balance data exists within the processor memory 243 or not.

If it is determined that corresponding white balance data exists within the processor memory 243, the processor CPU 242 in step S107 loads the corresponding white balance data from the processor memory 243. If it is determined that no corresponding white balance data exists within the processor memory 243, the processor CPU 242 exits the processing.

Then, the processor CPU 242 in step S108 performs white balance calculation processing by using the loaded corresponding white balance data and exits the processing.

In Japanese Unexamined Patent Application Publication No. 2005-131363, if no corresponding white balance data exists within the scope memory 214 and processor memory 243, processing ends.

On the other hand, an apparatus in Japanese Unexamined Patent Application No. 2003-265410 displays an error message if no corresponding white balance data exists and prompts a user to perform manual white balance processing. Then, the manual white balance processing is performed in response to the press of a W/B switch 244 (refer to FIG. 18) by a user based on the error message. After the manual white balance processing is performed, the white balance data associated with a light source ID and a scope ID is stored within the scope memory 214 and processor memory 243.

As described above, if corresponding white balance data exists within the scope memory 214, an optimum white balance in accordance with characteristics of a scope and light source used therewith can be obtained. If no corresponding white balance data exists within the scope memory 214 and corresponding white balance data exists within the processor memory 243, an optimum white balance in accordance with the characteristic of the scope can be obtained at least.

SUMMARY OF THE INVENTION

According to an aspect of the invention, there is provided an endoscopic apparatus including:

an endoscope that picks up an image of the inside of a tubular cavity;

a light source device that supplies illumination light to the endoscope and has light source identification information storage unit for storing light source identification information;

an image processing device that performs signal processing on image pickup signals from the endoscope and creates an endoscopic image, first white balance data storage unit for storing, for each of the light source identification information, white balance data to be used for white balance processing in the image processing device at least in association with the light source identification information;

second white balance data storage unit for storing white balance data to be used for white balance processing in the image processing device;

light source information extracting unit for extracting light source identification information of the light source device;

white balance data searching unit for searching white balance data associated with the light source identification information through the first white balance data storage unit based on the light source identification information of the light source device, which is extracted by the light source information extracting unit; and white balance data extracting unit for extracting white balance data stored in the second white balance data storage unit based on the result of the search by the white balance data searching unit.

The other features and advantages of the present invention will be sufficiently apparent from following descriptions.

BRIEF DESCRIPTION OF THE DRAWINGS

FIG. 2 is a diagram showing a memory configuration of the scope memory in FIG. 1 according to the first embodiment;

FIG. 12 is a diagram showing a memory configuration of the scope memory in FIG. 11 according to the second embodiment;

FIG. 19 is a diagram showing a memory configuration of the scope memory in FIG. 18;

FIG. 20 is a diagram showing a memory configuration of the processor memory in FIG. 18; and FIG. 21 is a flowchart illustrating an operation by the endoscopic system in FIG. 18.

DETAILED DESCRIPTION OF THE PREFERRED EMBODIMENTS

First Embodiment

Figure 1:
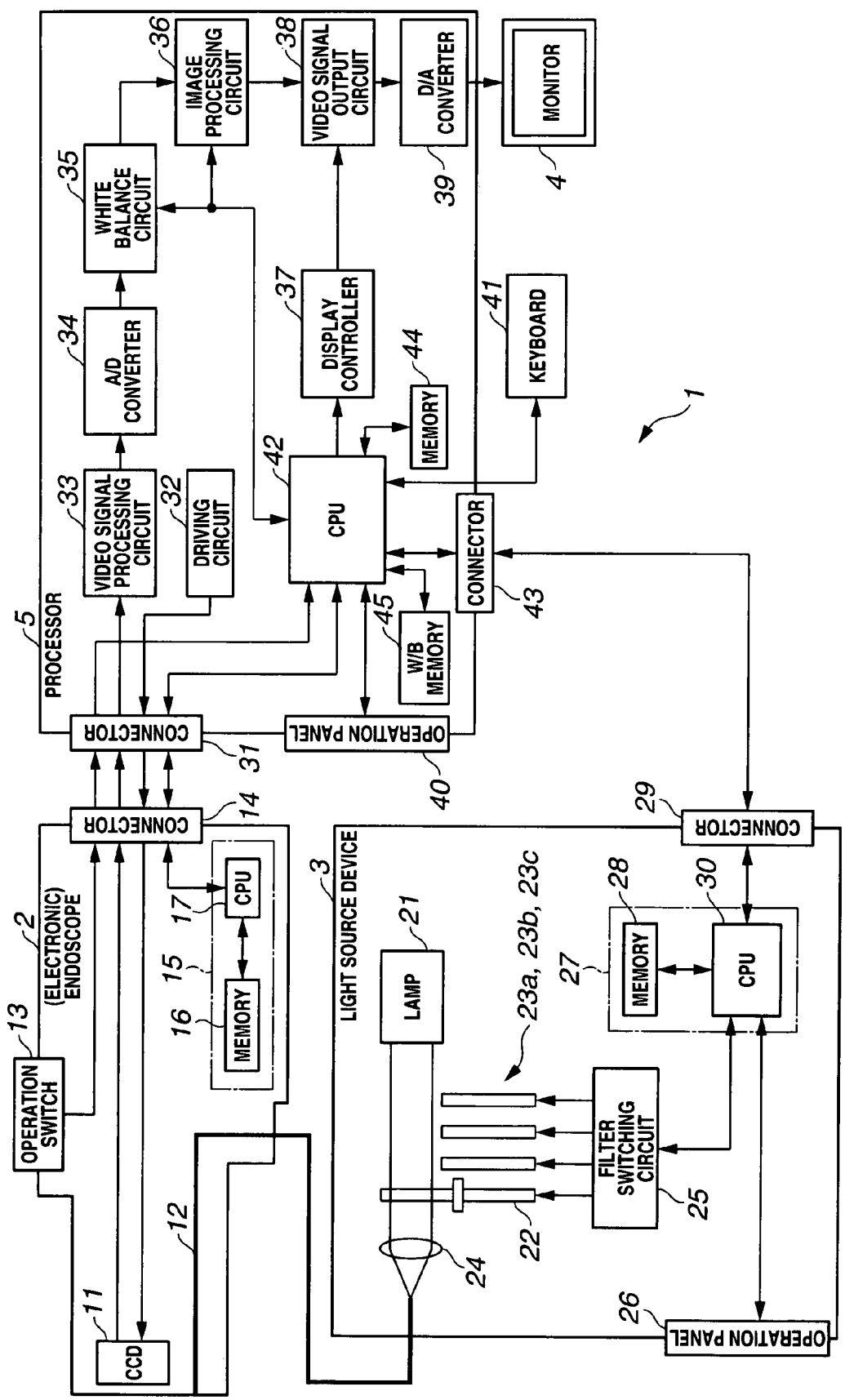
FIG. 1 is a block diagram showing a configuration of an endoscopic system according to a first embodiment of the present invention.

As shown in FIG. 1, an endoscopic system 1 according to this embodiment includes an (electronic) endoscope (also called scope) 2, a light source device 3 and a processor 5. The endoscope 2 is to be inserted into a body cavity to observe/treat an affected part. The light source device 3 supplies RGB light and special light to the endoscope 2. The processor 5 performs signal processing on endoscopic video signals picked up by the endoscope 2 and causes a monitor 4 to display an endoscopic image therefrom.

The endoscope 2 includes a CCD 11, a light guide 12, an operation switch 13 and an (electric) connector 14. The CCD 11 is a solid image pickup device at the distal end of an insertion section to be inserted into a body cavity of a patient. The light guide 12 guides observation illumination light to the distal end of the insertion section. The operation switch 13 is provided to an operation section for operating the endoscope. The connector 14 is provided to a connector section for connecting to the light source device 3 for connecting with the processor 5. A first storage circuit 15 is provided within the connector section. The connector 14 has identification unit (not shown) for identifying the CCD 11.

The first storage circuit 15 includes a non-volatile scope memory (such as EPROM and FRAM) 16 and a scope CPU 17. The scope memory 16 functions as endoscope identification information storage unit and second white balance data storage unit for storing data. The scope CPU 17 controls reading/writing data from/to the scope memory 16 and controls exchange (communication) of data with the processor 5.

The scope memory 16 has multiple storage areas (such as 14 storage areas). These storage areas store data, as shown in FIG. 2, as follows:

Area 1) scope serial No. (=scope ID);
Area 2) model name of endoscope (=scope model name data);
Area 3) size (=scope distal end diameter and forceps diameter data);
Area 4) CCD type (=CCD-related information (such as a number of pixels) data);
Area 5) number of times of energization (=numbers of times of connection of the endoscope to the processor and powering-on of the endoscope);
Area 6) user comment;
Area 7) first examination date (=date);
Area 8) warranty expiration date (=date);

Area 9) service comment;
Area 10) factory comment;
Area 11) reprocess information;
Area 12) number of times of inspection;
Area 13) version information; and
Area 14) sub-white-balance (=white balance data).

The white balance data in the sub-white-balance area of Area 14 is the white balance data, which is obtained when shipped from the factory or when manual white balance processing is performed thereon and is not associated with a light source ID.

The light source device 3 includes a lamp 21, an RGB filter 22, multiple, such as three, special light filters 23a, 23b and 23c, a collective lens 24, a filter switching device 25, an operation panel 26 and a second storage circuit 27. The lamp 21 emits white light for generating observation light. The RGB filter 22 is used for converting observation light from the lamp 21 to RGB frame sequential light. The special light filters 23a, 23b and 23c cut a specific wavelength of observation light from the lamp 21 and generate special light. The collective lens 24 collects observation light to an input end plane of the light guide 12. The filter switching device 25 switches the RGB filter 22 and special light filters 23a, 23b and 23c. The operation panel 26 is used for performing a setting operation. The RGB filter 22 and special light filters 23a, 23b and 23c construct an observation filter.

The second storage circuit 27 includes a non-volatile light source memory (such as an EEPROM and an FRAM) 28 that stores data and a light source CPU (control section) 30 that controls data reading/writing from/to the light source memory 28 and controls data exchange (communication) with the processor 5 through the connector 29. The light source CPU 30 also controls the filter switching device 25 and operation panel 26.

The light source memory 28 stores data including:
1) light source serial No. (=light source ID);
2) identification information of the special light filters in the light source device; and
3) usage data of light source device (such as number and time of use of the light source device, total lighting-up time of the lamp, total number/time of use of the RGB filter/special light filters).

Figure 3:
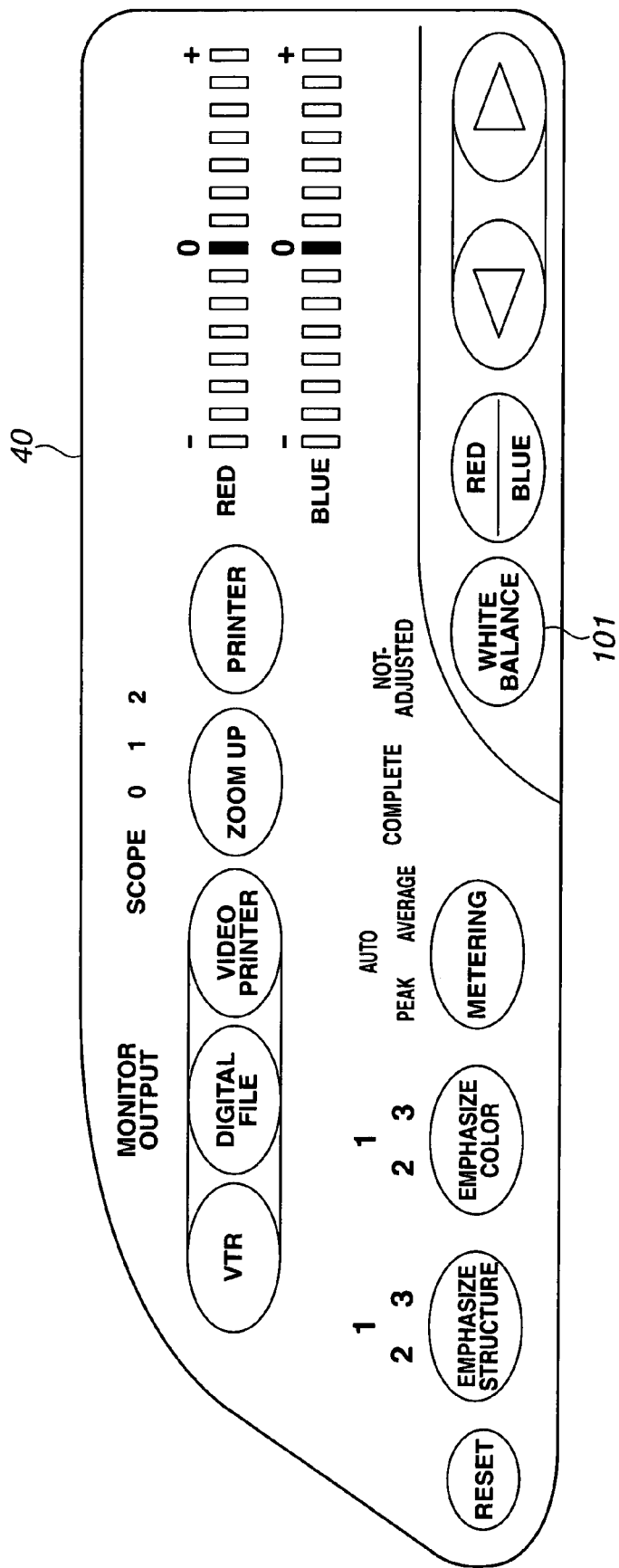
FIG. 3 is a diagram showing the operation panel of the processor in FIG. 1 according to the first embodiment.

The processor 5 includes a driving circuit 32, a video signal processing circuit 33, an A/D converting section 34, a white balance circuit 35, an image processing circuit 36, a display controller 37, a video signal output circuit 38, a D/A converting section 39, an operation panel 40 (refer to FIG. 3), a keyboard 41 and a processor CPU 42.

The driving circuit 32 is a circuit that drives the CCD 11 of the endoscope 2 through the connector 31.

The video signal processing circuit 33 is a circuit that performs signal processing on image pickup signals from the CCD 11 through the connector 31.

The A/D converting section 34 converts signals processed by the video signal processing circuit 33 to digital signals.

The white balance circuit 35 performs white balance processing on video signals converted to digital signals.

The image processing circuit 36 is a circuit that creates an endoscopic image to be displayed on the monitor 4 from video signals having undergone white balance processing.

The display controller 37 creates an image to be displayed on the monitor 4.

The video signal output circuit 38 is a circuit that synthesizes the output of the image processing circuit 36 and the output of the display controller 37 and outputs the result.

The D/A converting section 39 converts the output of the video signal output circuit 38 to analog signals and outputs the analog signals to the monitor 4.

The operation panel 40 and keyboard 41 have switches such as a W/B SW 101 for instructing manual white balance processing and are used for instructing operations.

The processor CPU 42 performs exchange of information with the operation panel 40 and keyboard 41, communication with the scope CPU 17 of the endoscope 2 through the connector 31, communication with the light source CPU 30 of the light source device 3 through the connector 43, and control of the white balance circuit 34, image processing circuit 36 and display controller 37.

Figure 4:
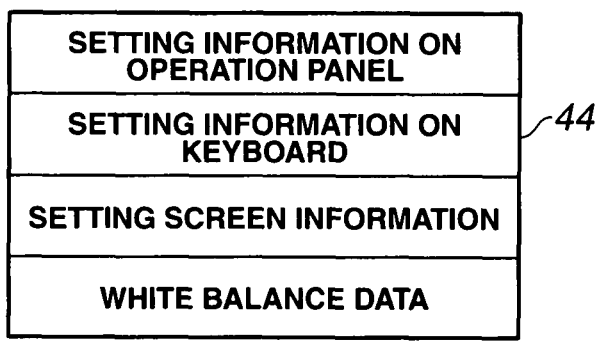
FIG. 4 is a diagram showing a memory configuration of the processor memory in FIG. 1 according to the first embodiment.
Figure 5:
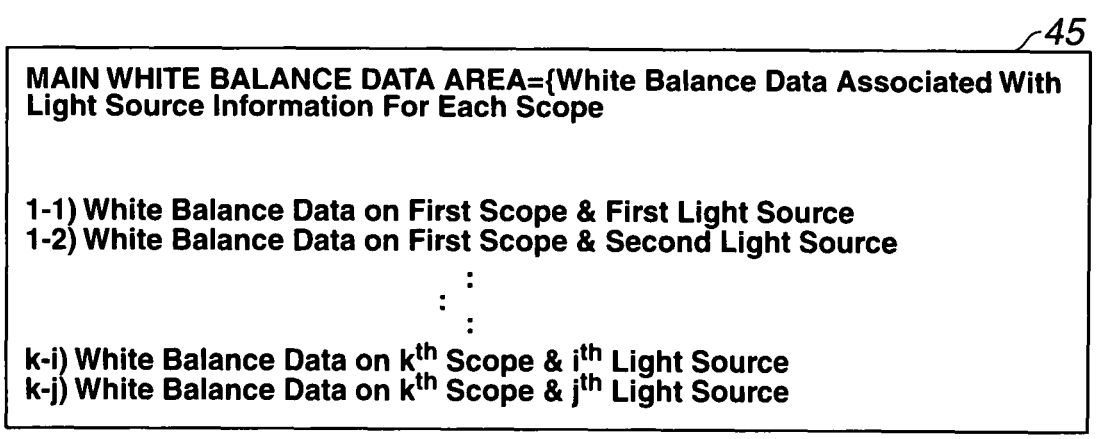
FIG. 5 is a diagram showing a memory configuration of the W/B memory in FIG. 1 according to the first embodiment.

The processor CPU 42 includes a processor memory 44 for backup and a W/B memory 45 functioning as first white balance data storage unit. The processor memory 44, as shown in FIG. 4, stores data including white balance data required for processing. The W/B memory 45, as shown in FIG. 5, has a main white balance data area that stores white balance data corresponding to the scope ID of the endoscope 2 and the light source ID of the light source device 3.

The white balance data stored in the main white balance data area is white balance data obtained when manual white balance processing is performed and is stored in association with the scope ID of the endoscope 2 and the light source ID of the light source device 3.

Figure 6:
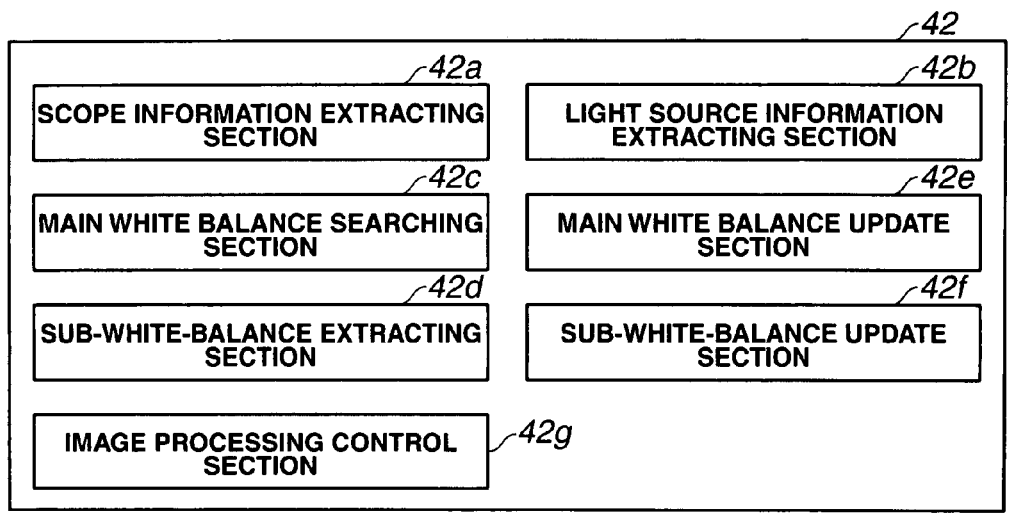
FIG. 6 is a functional block diagram showing a function configuration of the processor CPU in FIG. 1 according to the first embodiment.

The processor CPU 42 includes, as shown in FIG. 6, a scope information extracting section 42a, which functions as endoscope information extracting unit, a light source information extracting section 42b, which functions as light source information extracting unit, a main white balance data searching section 42c, which functions as white balance data searching unit, a sub-white-balance extracting section 42d, which functions as white balance data extracting unit, a main white balance update section 42e, a sub-white-balance update section 42f and an image processing control section 42g. According to the present embodiment, these components are implemented by software.

The scope information extracting section 42a is a function section that extracts a scope ID from the scope memory 16 (through the scope CPU 17). The light source information extracting section 42b is a function section that extracts a light source ID from the light source memory 28 (through the light source CPU 30). The main white balance searching section 42c is a function section that searches white balance data stored in the main white balance data area of the W/B memory 45 based on a light source ID. The sub-white-balance extracting section 42d is a function section that extracts white balance data in the sub-white-balance area from the scope memory 16 (through the scope CPU 17) if no corresponding white balance data exists in the main white balance data area of the W/B memory 45. The main white balance update section 42e is a function section that updates white balance data in the main white balance data area when manual white balance processing is performed. The sub-white-balance update section 42f is a function section that updates white balance data in the sub-white-balance data area when manual white balance processing is performed. The image processing control section 42g is a function section that controls each of the white balance circuit 35 and image processing circuit 38.

Figure 7:
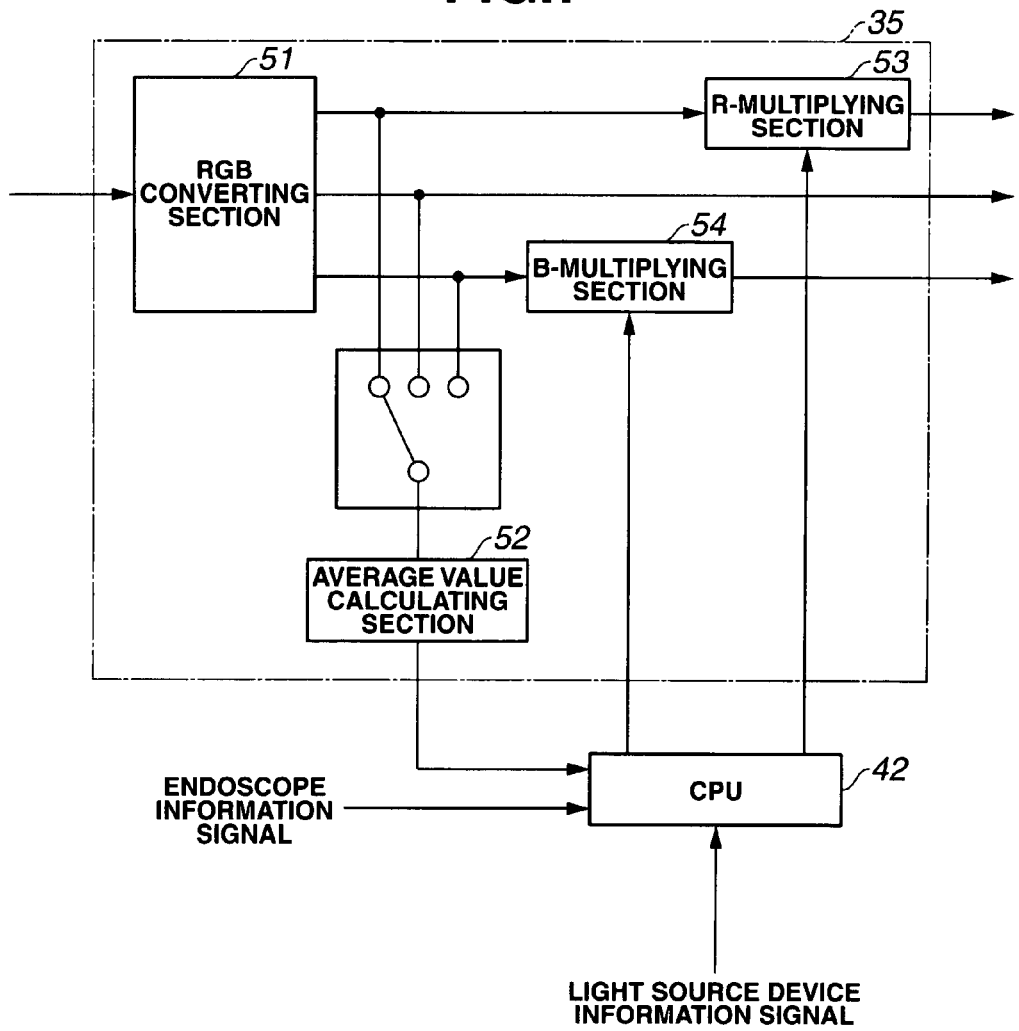
FIG. 7 is a block diagram showing a configuration of the white balance circuit in FIG. 1 according to the first embodiment.

The white balance circuit 35 includes, as shown in FIG. 7, an RGB converting section 51, an average value calculating section 52, an R-multiplying section 53 and a B-multiplying section 54. The RGB converting section 51 converts frame-sequential video signals, which have been converted to digital signals by the A/D converting section 34, to synchronization signals of RGB. The average value calculating section 52 calculates the average value of RGB signals. The R-multiplying section 53 multiplies an R-signal by a multiplication coefficient G/R from the CPU 42. The B-multiplying section 54 multiplies a B-signal by a multiplication coefficient G/B from the CPU 42. The white balance circuit 35 outputs signals of R:G:B=1:1:1 to the image processing circuit 36.

Next, operations by the endoscopic system 1 thus configured according to the embodiment will be described. For simple description, an example will be described in which the RGB filter 22 is only employed as an observation filter. However, the same effects may be provided by the special light filters 23a, 23b and 23c deployed on an optical path in addition to the RGB filter 22.

Figure 8:
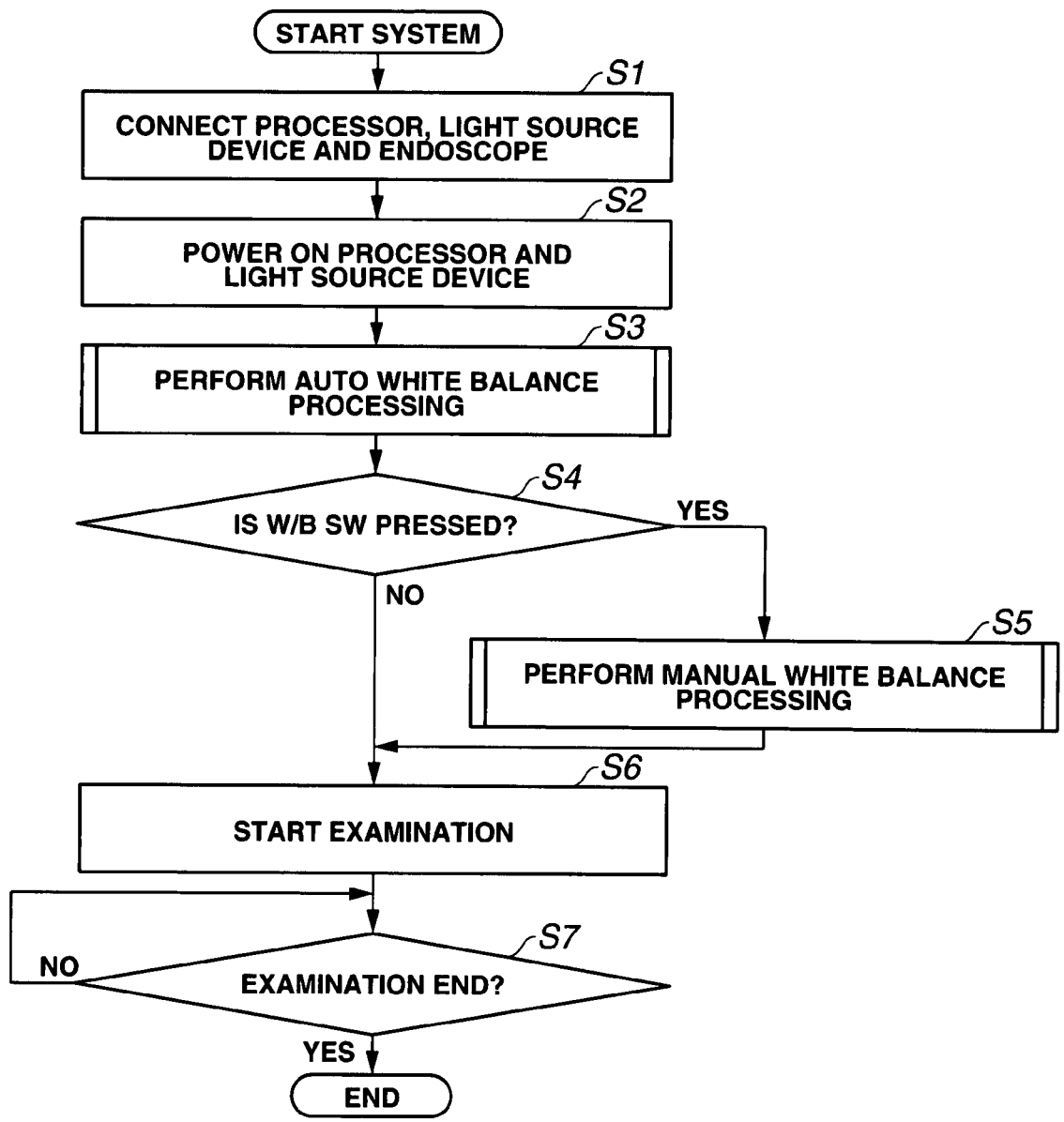
FIG. 8 is a flowchart illustrating an operation by the endoscopic system in FIG. 1 according to the first embodiment.

As shown in FIG. 8, the processor 5, scope (endoscope) 2 and light source device 3 are connected in step S1 and are powered on in step S2. In step S3, the processor CPU 42 in the processor 5 performs auto white balance processing. Details of the auto white balance processing will be described later.

After the auto white balance processing ends, the processor CPU 42 determines in step S4 whether the W/B SW 101 (refer to FIG. 3) on the operation panel 40 has been pressed or not. If it is determined that the W/B SW 101 has been pressed, the processor CPU 42 performs manual white balance processing, which will be described later, in step S5 and moves to step S6. If it is determined that the W/B SW 101 has not been pressed, the CPU 42 shifts the processing from step S4 to step S6 and starts an examination in step S6 and continues the examination until the detection of the end of the examination in step S7.

Figure 9:
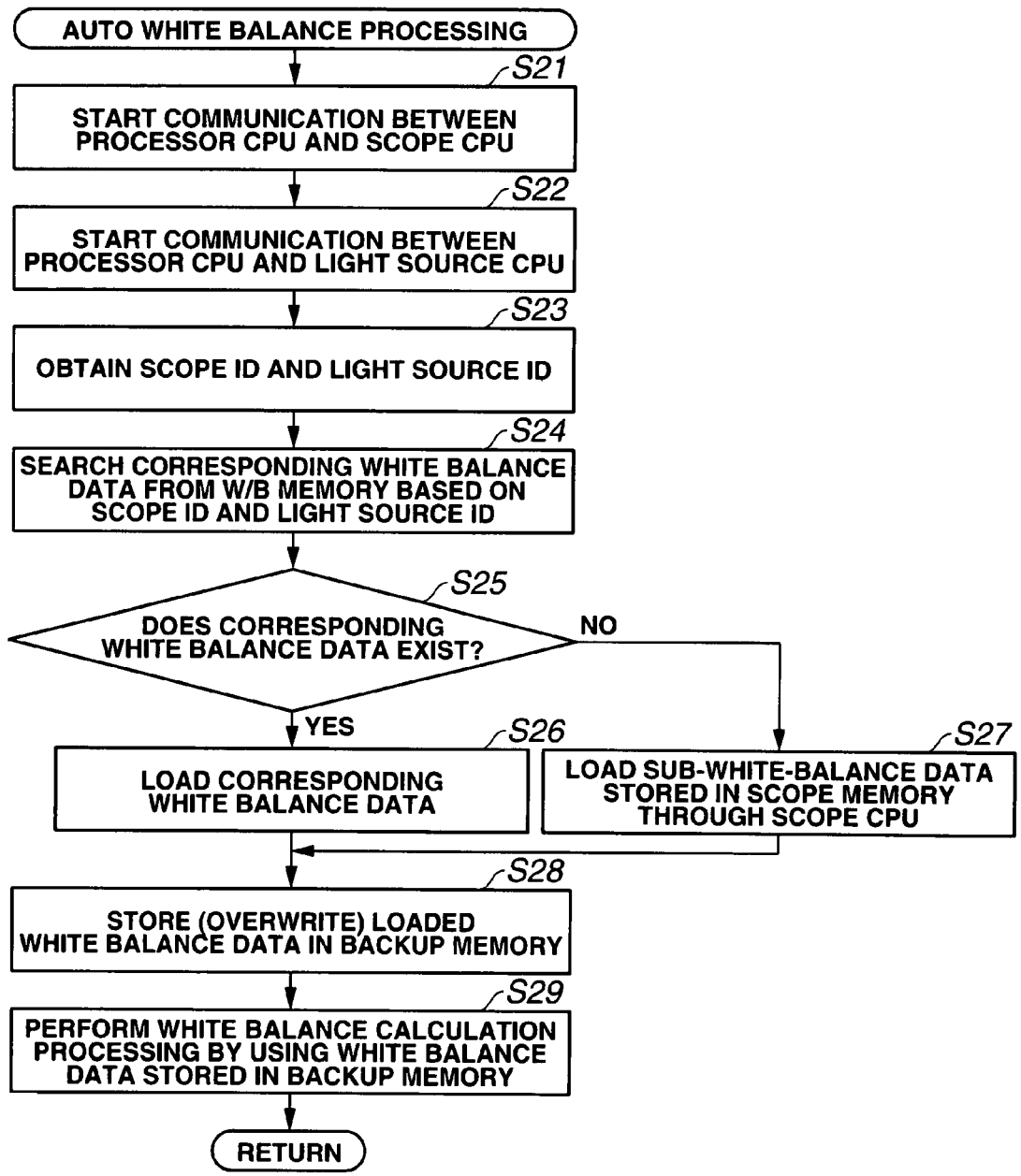
FIG. 9 is a flowchart showing a flow of the auto white balance processing in FIG. 6 according to the first embodiment.

Next, the auto white balance processing in step S3 will be described. As shown in FIG. 9, in the auto white balance processing, the processor CPU 42 starts communication with the scope CPU 17 in the scope 2 in step S21 and starts communication with the light source CPU 30 in the light source device 3 in step S22. Then, the processor CPU 42 in step S23 obtains the scope ID from the scope memory 16 by the function of the scope information extracting section 42a and the light source ID from the light source memory 28 by the function of the light source information extracting section 42b through the scope CPU 17 and light source CPU 30.

Next, the processor CPU 42 in step S24 searches corresponding white balance data (associating with the obtained scope ID and light source ID) through the main white balance area (refer to FIG. 5) of the W/B memory 45 based on the obtained scope ID and light source ID by the function of the main white balance searching section 42c. For example, if the scope ID=k and the light source ID=j, the white balance data of the $k^{th}$ scope and $j^{th}$ light source in FIG. 5 is the corresponding white balance data.

Then, the processor CPU 42 in step S25 determines whether any corresponding white balance data exists in the main white balance area or not. If corresponding white balance data exists, the processor CPU 42 in step S26 loads the corresponding white balance data from the W/B memory 45 and moves to step S28. On the other hand, if it is determined that no corresponding white balance data exists, the processor CPU 42 in step S27 loads white balance data (refer to FIG. 2) in the sub-white-balance area (Area 14) of the scope memory 16 through the scope CPU 17 by the function of the sub-white balance extracting section 42d and moves to step S28.

In step S28, the processor CPU 42 stores the loaded white balance data in the processor memory 44 for backup. If any data already exists in the white balance data area of the processor memory 44, the processor CPU 42 overwrites and stores the loaded white balance data.

Next, the processor CPU 42 in step S29 uses the white balance data in the white balance data area of the processor memory 44 to perform white balance calculation processing of adjusting the gains in the white balance circuit 35 by the function of the image processing control section 42g and exits the processing.

Figure 10:
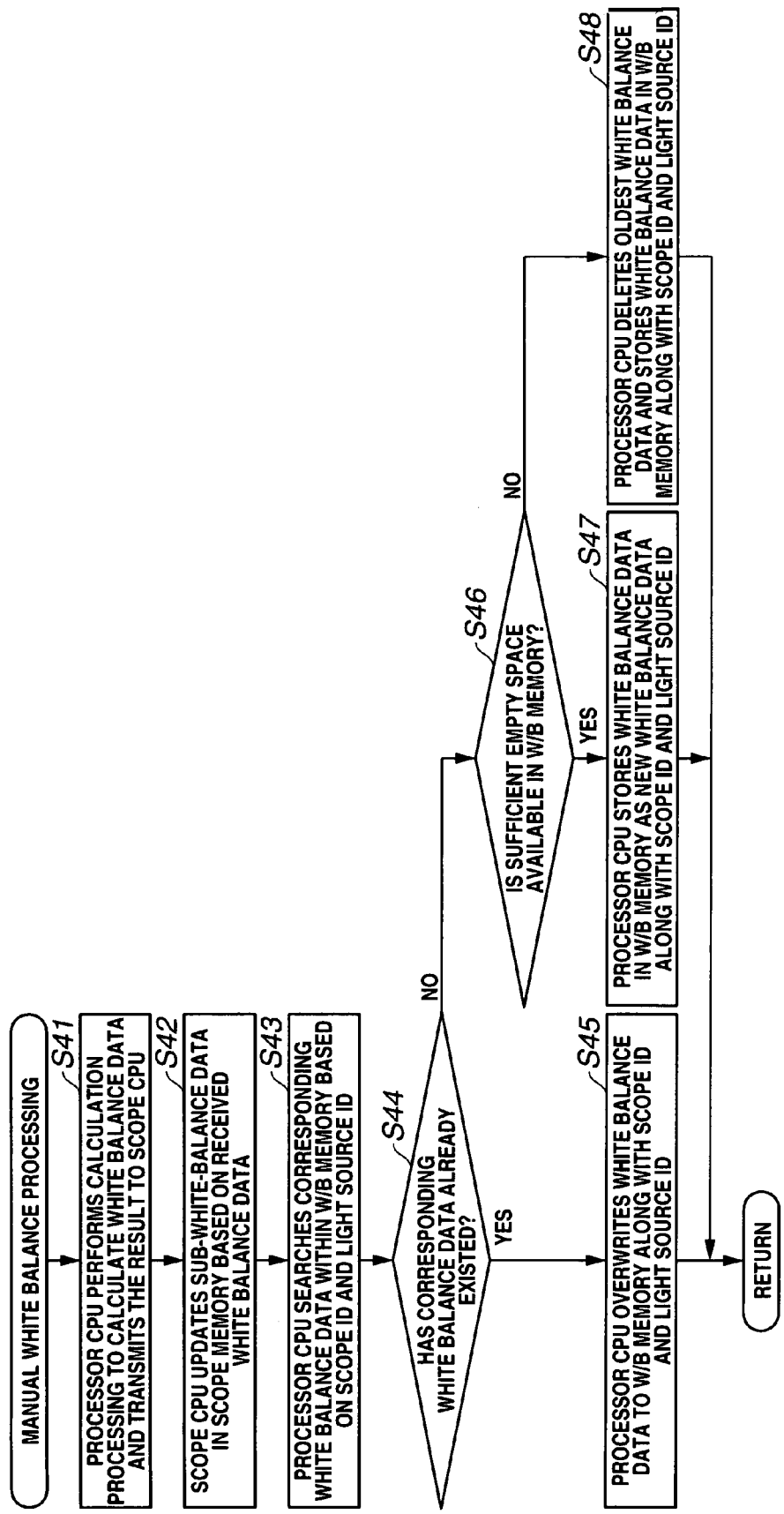
FIG. 10 is a flowchart showing a flow of the manual white balance processing in FIG. 6 according to the first embodiment.

Next, the manual white balance processing in step S5 described above will be described. In the manual white balance processing, the processor CPU 42 in step S41 performs calculation processing of calculating an average value of RGB signals in the average value calculating section 52 of the white balance circuit 35, calculates white balance data (G/R and G/B) and transmits the white balance data to the scope CPU 17, as shown in FIG. 10.

Then, in step S42, the scope CPU 17 instructs the sub-white-balance update section 42f of the processor CPU 42 to update the white balance data in the sub-white-balance area with the received white balance data.

Next, in step S43, the processor CPU 42 searches-corresponding white balance data through the main white balance area of the W/B memory 45 based on the scope ID and light source ID by the function of the main white balance searching section 42c.

Then, the processor CPU 42 in step S44 determines whether any corresponding white balance data exists in the main white balance area or not. If the corresponding white balance data exists, the processor CPU 42 in step S45 overwrites the white balance data calculated in step S41 along with the scope ID and light source ID and updates the main white balance area of the W/B memory 45 by the function of the main white balance update section 42e.

If it is determined that no corresponding white balance data exists in the main white balance area, the processor CPU 42 in step S46 determines whether any sufficient empty space (predetermined empty space) is available in the main white balance area of the W/B memory 45 or not by the function of the main white balance update section 42e.

If it is determined that the main white balance area of the W/B memory 45 has a sufficient empty space (predetermined empty space) available, the processor CPU 42 in step S47 stores the white balance data calculated in step S41 along with the scope ID and light source ID in the main white balance area of the W/B memory 45 by the function of the main white balance update section 42e.

On the other hand, if it is determined that no sufficient empty space (predetermined empty space) is available in the main white balance area of the W/B memory 45, the processor CPU 42 in step S48 deletes the oldest white balance data and stores the white balance data calculated in step S41 along with the scope ID and light source ID in the main white balance area of the W/B memory 45 by the function of the main white balance update section 42e.

In this way, according to the present embodiment, white balance data is stored in the main white balance area on the processor 5 side in association with the scope ID and light source ID while the latest white balance data used by the scope 2 is stored in the sub-white-balance area on the scope 2 side.

Thus, when the processor 5, scope 2 and light source device 3 are connected, the processor CPU 42 of the processor 5 can perform white balance processing by loading corresponding white balance data from the main white balance area of the W/B memory 45 if the combination of the connected scope 2 and light source device 3 has been used. Therefore, an endoscopic image can be obtained in optimum color.

Even if the combination of the connected scope 2 and light source device 3 has not been used, the processor CPU 42 of the processor 5 can perform white balance processing by loading white balance data in the sub-white-balance area of the scope memory 16. Therefore, the lately used white balance data can be used in accordance with the characteristic of the scope 2 at least, and an endoscopic image in good color can be obtained.

Second Embodiment

Since a second embodiment is almost identical to the first embodiment, only differences therebetween will be described. The same reference numerals are given to the same components, the description of which will be omitted herein.

Figure 11:
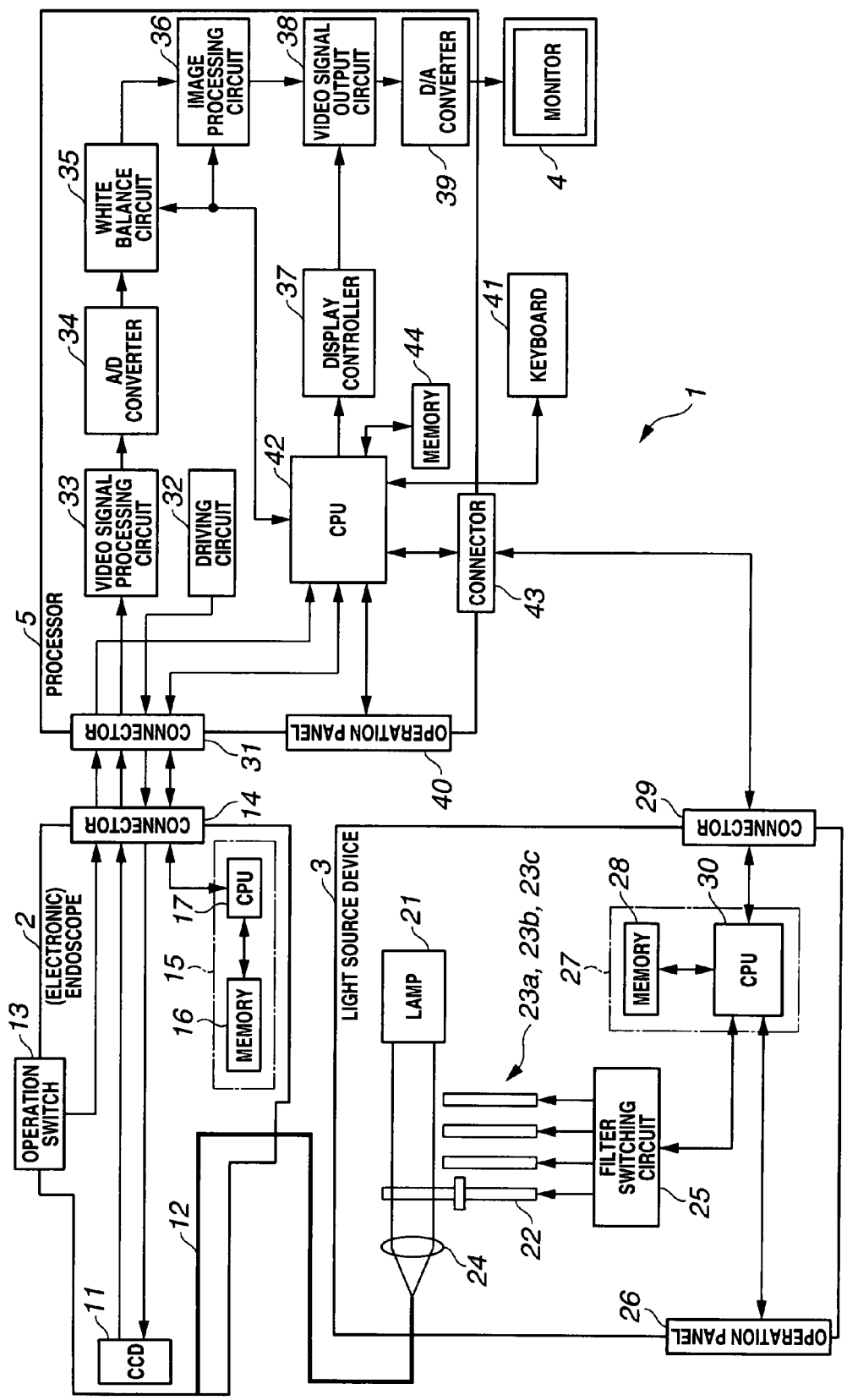
FIG. 11 is a block diagram showing a configuration of an endoscopic system according to a second embodiment of the present invention.

The present embodiment is different from the first embodiment in that the W/B memory 45 of the processor 5 is omitted as shown in FIG. 11 and that the white balance data in the main white balance area of the W/B memory 45 is stored in Area 15 of the scope memory 16 as shown in FIG. 12.

Figure 13:
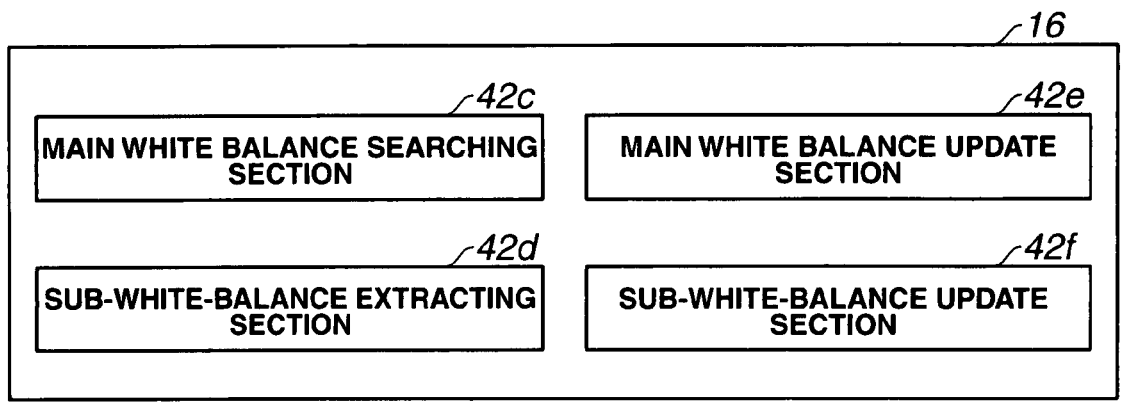
FIG. 13 is a functional block diagram showing a functional configuration of the scope CPU in FIG. 11 according to the second embodiment.
Figure 14:
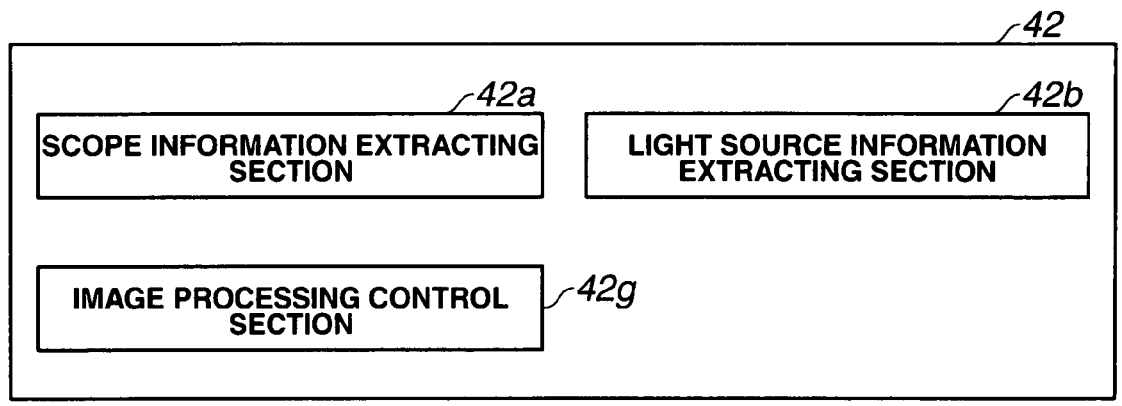
FIG. 14 is a functional block diagram showing a functional configuration of the processor CPU in FIG. 11 according to the second embodiment.

As shown in FIGS. 13 and 14, the main white balance searching section 42c, sub-white-balance extracting section 42d, main white balance update section 42e and sub-white-balance update section 42f in the processor CPU 42 according to the first embodiment are provided in the scope CPU 16. The rest of the configuration is the same as that of the first embodiment.

Figure 15:
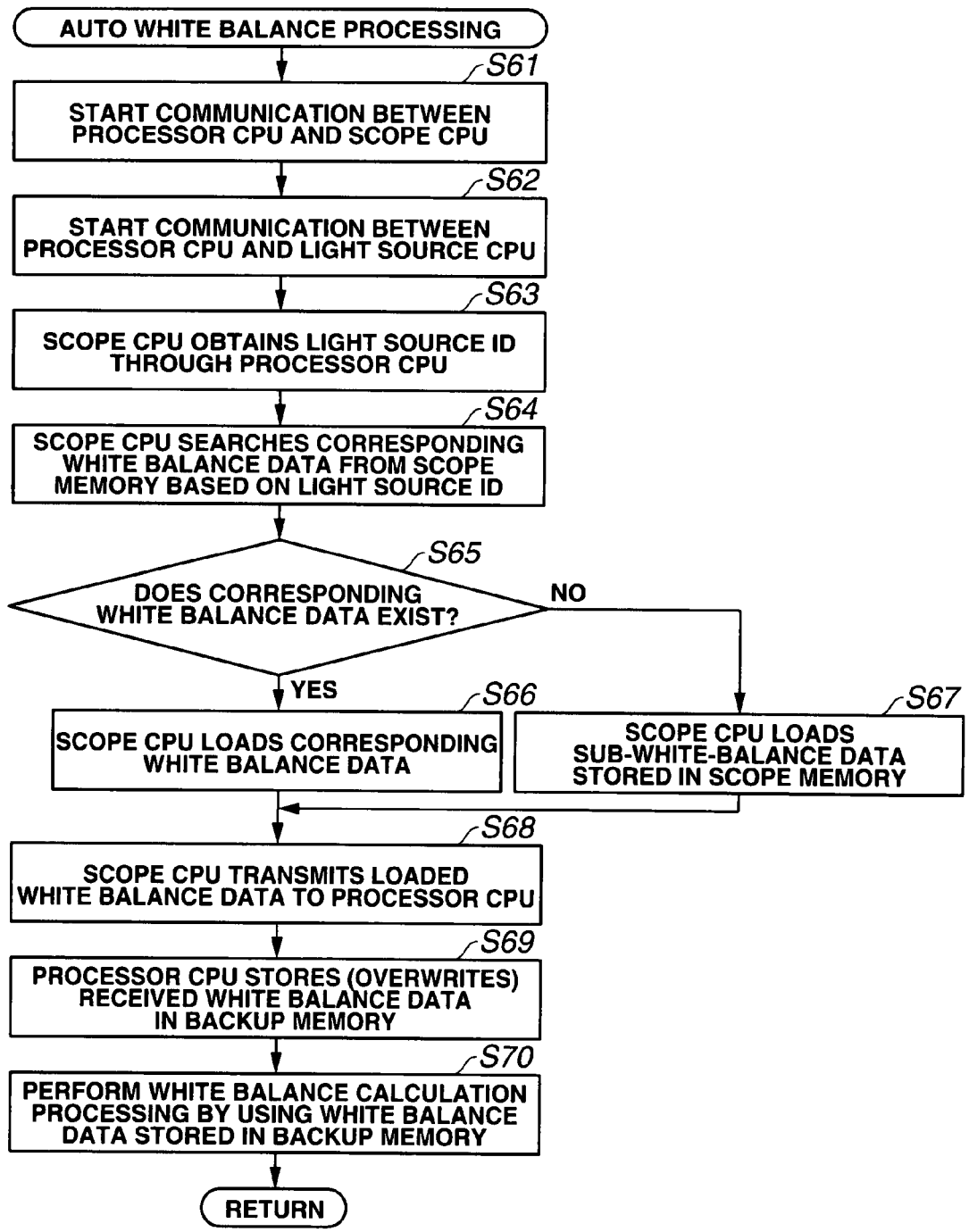
FIG. 15 is a flowchart showing a flow of auto white balance processing by the endoscopic system in FIG. 11 according to the second embodiment.

The auto-white balance processing in the present embodiment thus configured will be described. As shown in FIG. 15, the processor CPU 42 starts communication with the scope CPU 17 in the scope 2 in step S61 and starts communication with the light source CPU 30 in the light source device 3 in step S62. Then, the scope CPU 17 in step S63 obtains the light source ID from the light source memory 28 by the function of the light source information extracting section 42b of the processor CPU 42 through the processor CPU 42.

Next, the scope CPU 17 in step S64 searches corresponding white balance data (associating with the obtained light source ID) through the main white balance area (Area 15) of the scope memory 16 based on the obtained light source ID by the function of the main white balance searching section 42c. For example, if the light source ID=j, the white balance data of $j^{th}$ light source in FIG. 12 is the corresponding white balance data.

Then, the scope CPU 17 in step S65 determines whether any corresponding white balance data exists in the main white balance area or not. If corresponding white balance data exists, the scope CPU 17 in step S66 loads the corresponding white balance data from the scope memory 16 and moves to step S68. On the other hand, if it is determined that no corresponding white balance data exists, the scope CPU 17 in step S67 loads white balance data (refer to FIG. 12) in the sub-white-balance area (Area 14) of the scope memory 16 by the function of the sub-white balance extracting section 42d and moves to step S68.

In step S68, the scope CPU 17 transmits the loaded white balance data to the processor CPU 42.

Then, the processor CPU 42 stores the white balance data received in step S69 in the processor memory 44 for backup. If any data already exists in the white balance data area of the processor memory 44, the processor CPU 42 overwrites and stores the received white balance data.

Next, the processor CPU 42 in step S70 uses the white balance data in the white balance data area of the processor memory 44 to perform white balance calculation processing of adjusting the gains in the white balance circuit 35 by the function of the image processing control section 42g and exits the processing.

Figure 16:
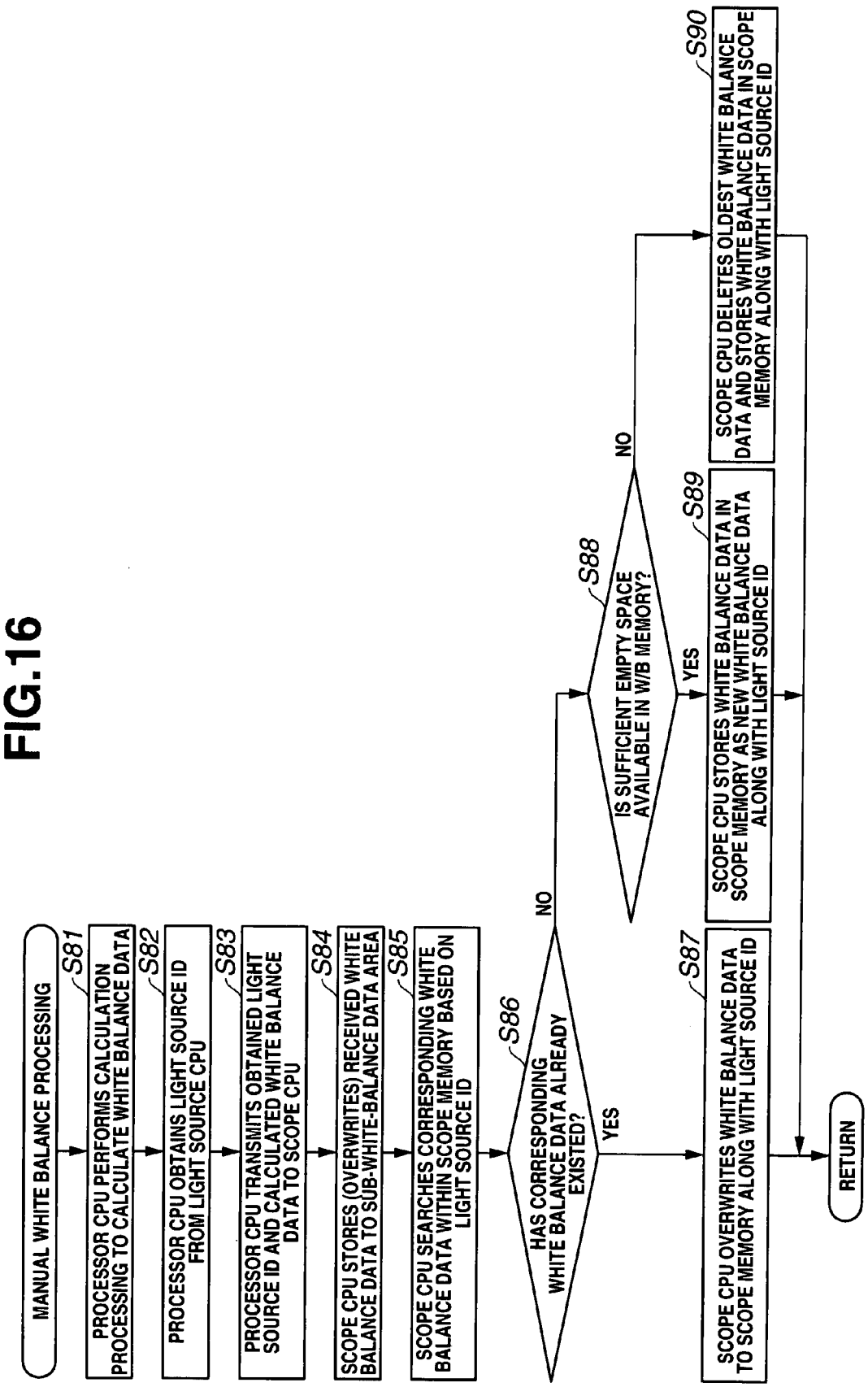
FIG. 16 is a flowchart showing a flow of manual white balance processing by the endoscopic system in FIG. 11 according to the second embodiment.

Next, manual white balance processing according to the present embodiment will be described. In the manual white balance processing, the processor CPU 42 in step S81 performs calculation processing of calculating an average value of RGB signals in the average value calculating section 52 of the white balance circuit 35 and the like and calculates white balance data (G/R and G/B), as shown in FIG. 16.

Next, the processor CPU 42 in step S82 obtains the light source ID from the light source memory 28 by the function of the light source information extracting section 42b.

Then, in step S83, the processor CPU 42 transmits the obtained light source ID and the calculated white balance data to the scope CPU 16.

Then, in step S84, the scope CPU 16 updates the white balance data in the sub-white-balance area (Area 15) with the received white balance data by the function of the sub-white-balance update section 42f.

Next, in step S85, the scope CPU 16 searches corresponding white balance data through the main white balance area (Area 15) of the scope memory 17 based on the light source ID by the function of the main white balance searching section 42c.

Then, the scope CPU 16 in step S86 determines whether any corresponding white balance data exists in the main white balance area or not. If the corresponding white balance data exists, the scope CPU 16 in step S87 overwrites the white balance data calculated in step S81 along with the light source ID and updates the main white balance area (Area 15) of the scope memory 17 by the function of the main white balance update section 42e.

If it is determined that no corresponding white balance data exists in the main white balance area (Area 15), the scope CPU 16 in step S88 determines whether any sufficient empty space (predetermined empty space) is available in the main white balance area (Area 15) of the scope memory 17 or not by the function of the main white balance update section 42e.

If it is determined that the main white balance area of the scope memory 17 has a sufficient empty space (predetermined empty space) available, the scope CPU 16 in step S89 stores the white balance data calculated in step S81 along with the light source ID in the main white balance area (Area 15) of the scope memory 17 by the function of the main white balance update section 42e.

On the other hand, if it is determined that no sufficient empty space (predetermined empty space) is available in the main white balance area (Area 15) of the scope memory 17, the scope CPU 16 in step S90 deletes the oldest white balance data and stores the white balance data calculated in step S81 along with the light source ID in the main white balance area (Area 15) of the scope memory 17 by the function of the main white balance update section 42e.

In this way, in addition to the effects of the first embodiment, white balance data is stored in the main white balance area of the scope memory 17 only in association with the light source ID, eliminating the necessity for the W/B memory 45 on the processor 5 side, according to the present embodiment. Therefore, the main white balance area of the scope memory 17 only requires a smaller space than that of the main white balance area of the W/B memory 45, and corresponding white balance data can be searched inexpensively and quickly.

Having described that white balance data in the sub-white balance area is updated when manual white balance processing is performed according to the present embodiment, like the first embodiment, the present invention is not limited thereto. For example, white balance data in the sub-white-balance area may be updated with corresponding white balance data if the corresponding white balance data exists as a result of the search through the main white balance area (Area 15).

In the auto white balance processing in this case, the scope CPU 16 transmits a signal indicating that the search has been completed to the processor CPU 42, and the processor CPU 42 receives the completion signal. Then, the white balance data in the sub-white-balance area of the scope memory 17 is loaded, and white balance processing is performed thereon. Thus, the same effects as those of the present embodiment can be obtained, and the processing in steps S65 to S67 in FIG. 15 can be omitted.

Figure 17:
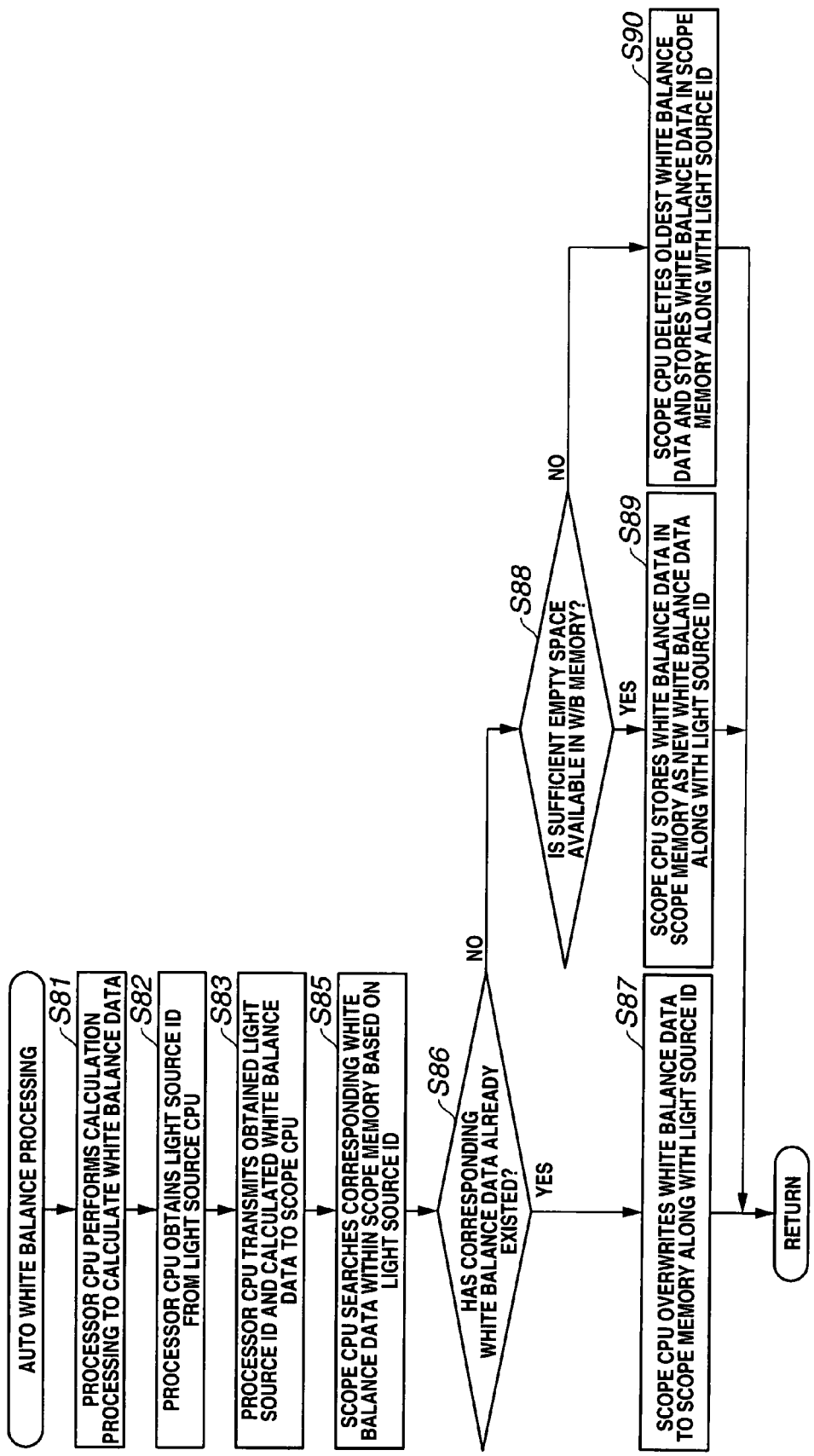
FIG. 17 is a flowchart showing a flow of a variation example of the auto white balance processing by the endoscopic system in FIG. 11 according to the second embodiment.
Figure 18:
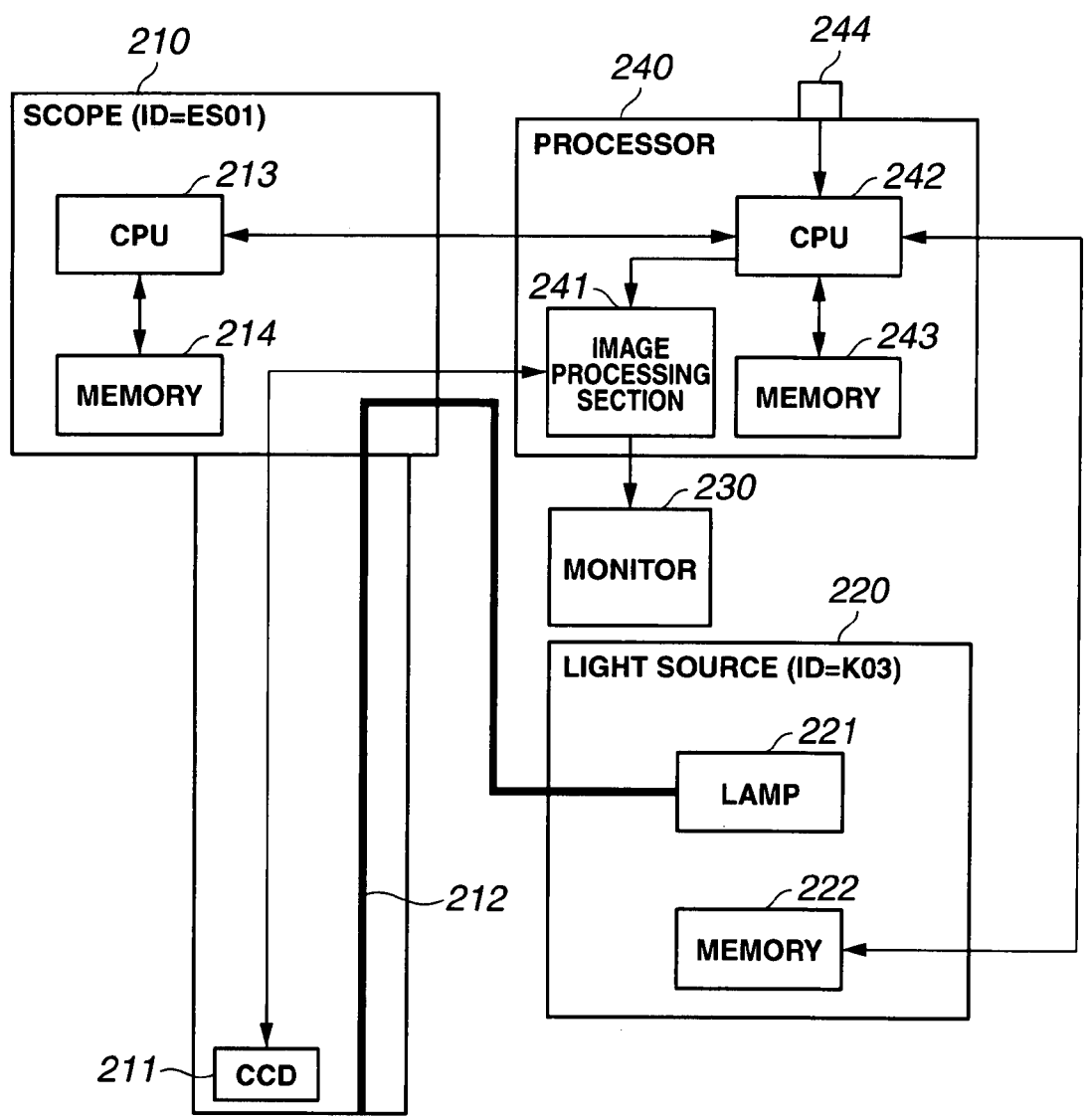
FIG. 18 is a block diagram showing a configuration of a conventional endoscopic system.

Having described that, according to the above-described embodiment, white balance data in the sub-white-balance area is updated, the present invention is not limited thereto. White balance data in the sub-white-balance area may be disabled to update as fixed data. Thus, if no corresponding white balance data exists as a result of the search, white balance processing can be performed by using fixed white balance data (such as reference white balance data) independent of the light source device connected thereto. In this case, the flow of the auto white balance processing is as in FIG. 17.

It is apparent that wide variety of different embodiments of the present invention can be configured based on the present invention without departing from the spirit and scope of the present invention. The present invention is not limited by specific embodiments but the appended claims.

What is claimed is:

1. An endoscopic apparatus comprising:
an endoscope comprising:
   an image pickup device configured to convert an object image to an image signal, and
   an endoscope identification information storage unit configured to store endoscope identification information for identifying the endoscope;
a light source device configured to supply illumination light to the endoscope, the light source device comprising a light source identification information storage unit configured to store light source identification information for identifying the light source device;
a first white balance data storage unit provided in a processor to which the endoscope and the light source device are connected and configured to store one or more white balance data, wherein each of the white balance data stored in the first white balance data storage unit is associated with predetermined light source identification information for identifying a predetermined light source device and predetermined endoscope identification information for identifying a predetermined endoscope;
a second white balance data storage unit provided in the endoscope, the second white balance data storage unit configured to store white balance data not associated with any light source identification information;
a white balance data source determination unit configured to determine whether white balance data associated with the light source identification information for identifying the light source device and the endoscope identification information for identifying the endoscope exists in the first white balance data storage unit;
a white balance processing unit configured to perform white balance processing on the image signal, wherein:
   if the white balance data source determination unit determines that white balance data associated with the light source identification information for identifying the light source device and the endoscope identification information for identifying the endoscope does exist in the first white balance data storage unit, the white balance processing unit performs white balance processing using such white balance data, and
   if the white balance data source determination unit determines that white balance data associated with the light source identification information for identifying the light source device and the endoscope identification information for identifying the endoscope does not exist in the first white balance data storage unit, the white balance processing unit performs white balance processing using the latest white balance data in accordance with at least a characteristic of the endoscope, the latest white balance data having been obtained in advance and stored in the second white balance data storage unit provided in the endoscope:
a white balance switch for performing manual white balance processing;
means configured to calculate white balance data and update the white balance data in the second white balance data storage unit, when the white balance switch is pressed;
a second white balance data source determination unit configured to determine, when the white balance switch is pressed, whether white balance data, which corresponds to the endoscope identification information and the light source identification information at the time that the white balance switch is pressed, exists in the first white balance data storage unit; and
means configured to, when corresponding white balance data does not exist in the first white balance data storage unit as a result of determination in the second white balance data source determination unit, store the white balance data updated in the second white balance data storage unit along with the endoscope identification information and the light source identification information, in the first white balance data storage unit, and configured to, when corresponding white balance data exists in the first white balance data storage unit, update the white balance data in the first white balance data storage unit by writing the white balance data updated in the second white balance data storage unit along with the endoscope identification information and the light source identification information over the white balance data in the first white balance data storage unit.

2. The endoscopic apparatus according to claim 1, wherein:
the first white balance data storage unit stores white balance data to be used for the white balance processing in the processor in association with the light source identification information and the endoscope identification information and for each of the light source identification information and the endoscope identification information; and
the white balance data source determination unit determines existence of white balance data associated with the light source identification information and the endoscope identification information through the first white balance data storage unit based on the light source identification information of the light source device, which is stored in the light source identification information storage unit, and the endoscope identification information, which is stored in the endoscope information storage unit.

3. The endoscopic apparatus according to claim 2, wherein:
the processor has a white balance processing execution instructing unit; and
when white balance processing is instructed by the white balance processing execution instructing unit, white balance data, which is not associated with the light source identification information, is overwritten and stored in the second white balance data storage unit.

4. The endoscopic apparatus according to claim 2, wherein the white balance data stored in the second white balance data storage unit is a fixed value, which is not overwritable.

5. The endoscopic apparatus according to claim 1, wherein:
the processor has a white balance processing execution instructing unit; and
when white balance processing is instructed by the white balance processing execution instructing unit, white balance data, which is not associated with the light source identification information, is overwritten and stored in the second white balance data storage unit.

6. The endoscopic apparatus according to claim 1, wherein the white balance data stored in the second white balance data storage unit is a fixed value, which is not overwritable.

7. A control method for an endoscopic apparatus, the endoscopic apparatus comprising:
an endoscope comprising:
an image pickup device configured to convert an object image to an image signal, and
an endoscope identification information storage unit configured to store endoscope identification information for identifying the endoscope; and
a light source device configured to supply illumination light to the endoscope, the light source device comprising a light source identification information storage unit configured to store light source identification information for identifying the light source device;
the method comprising:
a first white balance data storage step of storing each white balance data associated with predetermined light source identification information for identifying a predetermined light source device and predetermined endoscope identification information for identifying a predetermined endoscope in a first white balance data storage unit that is provided in a processor to which the endoscope and the light source device are connected and is configured to store one or more white balance data associated with the light source identification information and the endoscope identification information;
a second white balance data storage step of storing white balance data not associated with any light source identification information in a second white balance storage unit provided in the endoscope and configured to store the white balance data not associated with any light source identification information;
a white balance data source determining step of determining whether white balance data associated with the light source information for identifying the light source device and the endoscope identification information for identifying the endoscope exists in the first white balance data storage unit;
a white balance processing step of performing white balance processing on the image signal, wherein
if the white balance data source determining step determines that white balance data associated with the light source identification information for identifying the light source device and the endoscope identification information for identifying the endoscope does exist in the first white balance data storage unit, the white balance processing is performed using such white balance data in the white balance processing step, and
if the white balance data source determining step determines that white balance data associated with the light source identification information for identifying the light source device and the endoscope identification information for identifying the endoscope does not exist in the first white balance data storage unit, the white balance processing is performed using the latest white balance data in accordance with at least a characteristic of the endoscope, the latest white balance data having been obtained in advance and stored in the second white balance data storage unit provided in the endoscope in the white balance processing step;
a step of operating a white balance switch for performing manual white balance processing;
a step of calculating white balance data and updating the white balance data in the second white balance data storage unit, when the white balance switch is pressed;
a second white balance data source determining step of determining, when the white balance switch is pressed, whether white balance data, which corresponds to the endoscope identification information and the light source identification information at the time that the white balance switch is pressed, exists in the first white balance data storage unit; and
a step of storing, when corresponding white balance data does not exist in the first white balance data storage unit as a result of determination in the second white balance data source determining step, the white balance data updated in the second white balance data storage unit along with the endoscope identification information and the light source identification information, in the first white balance data storage unit, and updating, when corresponding white balance data exists in the first white balance data storage unit, the white balance data in the first white balance data storage unit by writing the white balance data updated in the second white balance data storage unit along with the endoscope identification information and the light source identification information over the white balance data in the first white balance data storage unit.

8. The control method for the endoscopic apparatus according to claim 7, wherein:
the first white balance data storage step stores white balance data to be used for the white balance processing in the processor in association with the light source identification information and the endo scope identification information and for each of the light source identification information and the endoscope identification information; and
the white balance data source determining step determines existence of white balance data associated with the light source identification information and the endoscope identification information through the first white balance data storage unit based on the light source identification information of the light source device, which is stored in the light source identification information storage unit, and the endoscope identification information, which is stored in the endoscope information storage step.

9. The control method for the endoscopic apparatus according to claim 8, wherein:
the processor has a white balance processing execution instructing unit; and
when white balance processing is instructed by the white balance processing execution instructing unit, white balance data, which is not associated with the light source identification information, is overwritten and stored in the second white balance data storage unit.

10. The control method for the endoscopic apparatus according to claim 8, wherein the white balance data stored in the second white balance data storage unit is a fixed value, which is not overwritable.

11. The control method for the endoscopic apparatus according to claim 7, wherein:
   the processor has a white balance processing execution instructing unit; and
   when white balance processing is instructed by the white balance processing execution instructing unit, white balance data, which is not associated with the light source identification information, is overwritten and stored in the second white balance data storage unit.

12. The control method for the endoscopic apparatus according to claim 7, wherein the white balance data stored in the second white balance data storage unit is a fixed value, which is not overwritable.

* * * * *